United States Patent [19]

Kidd et al.

[11] Patent Number: 4,533,321
[45] Date of Patent: Aug. 6, 1985

[54] BRAIDED ELASTOMER ORTHODONTIC TENSIONING DEVICE

[75] Inventors: Patrick D. Kidd, San Dimas; Terry L. Sterrett, Long Beach; Craig A. Andreiko, Alta Loma, all of Calif.

[73] Assignee: Sybron Corporation, Rochester, N.Y.

[21] Appl. No.: 605,892

[22] Filed: May 1, 1984

[51] Int. Cl.³ .............................................. A61C 3/00
[52] U.S. Cl. ...................................... 433/18; 433/11
[58] Field of Search ....................... 433/18, 19, 11, 13, 433/15; 206/805; 128/335.5

[56] References Cited

U.S. PATENT DOCUMENTS

| | | | |
|---|---|---|---|
| 3,091,856 | 6/1963 | Goldstein | 433/18 |
| 3,123,913 | 3/1964 | Rubin | 433/20 |
| 3,839,524 | 10/1974 | Adams et al. | 128/335.5 |
| 3,961,421 | 6/1976 | Wallshein | 433/18 |
| 4,321,038 | 3/1982 | Porteous | 433/136 |

Primary Examiner—John J. Wilson
Attorney, Agent, or Firm—Robert A. Gerlach; Robert J. Bird

[57] ABSTRACT

An orthodontic tensioning thread comprising a plurality of elastomeric strands braided together, the combined effect of the braid providing significantly improved tensile strength, elasticity retention, tieability and knot retention as compared to prior art monofilaments of comparable circumference.

4 Claims, 6 Drawing Figures

BRAIDED ELASTOMER ORTHODONTIC TENSIONING DEVICE

BACKGROUND AND SUMMARY OF THE INVENTION

The subject matter of this invention relates to orthodontic apparatus and more particularly to intraoral tensioning devices for the purpose of imparting forces to the teeth.

Intraoral elastics have been used by the orthodontic profession for a number of years. The most advanced elastics are generally considered to be those based on urethane elastomers which are molded or extruded into thread, tubes, chain, or small O-rings for ligation.

The primary purpose of the devices (other than the O's) is to move teeth by tensioning the devices between two or several teeth. The polyurethane has been used due to its stability in the oral environment, high strength, and relative high tensile modulus and tear resistance and ease of processing compared to other elastomers such as natural rubber, styrene butadiene rubbers (SBR's), or silicones. A prominent drawback, however, has been the low creep resistance and poor force retention over the normal span between office visits (4–6 weeks). This problem has rendered devices such as the elastic thread, chain or tube, of reduced utility in cases where a steady, long-term force is needed for the best treatment results. Used in such cases now are either steel springs, which can cause considerable patient discomfort, or natural rubber bands which must be replaced by the patient on a daily basis between appointments with the orthodontist.

This invention relates to a novel braided elastic thread which maintains a much greater percentage of its initial force over the normal 6-week period between office visits. The braided thread can be tied into loops and other orthodontically useful shapes to effect tooth movement. The braided form allows these superior properties even where the rubber used to produce each strand of the braid is the same as for the traditional monofilament, molded or extruded product.

DRAWING

DESCRIPTION

Figure 1:
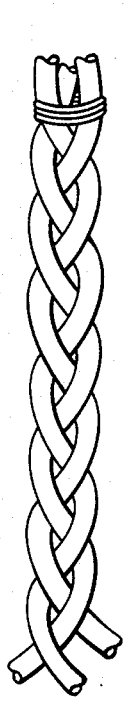
FIG. 1 shows a standard braid of three individual strands.
Figure 2:
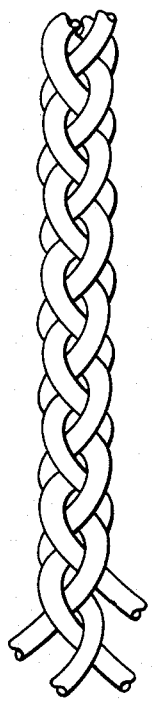
FIG. 2 shows a braid of four individual strands.
Figure 3:
FIG. 3 shows a braid of eight strands braided in a "two-over-one" pattern.
Figure 4:
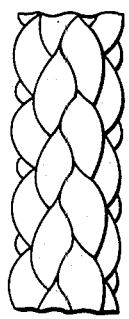
FIG. 4 shows a braid of eight strands braided in a "one-over-one" pattern.
Figure 5:
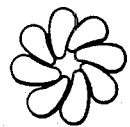
FIG. 5 shows the cross section of an eight strand braid.

With reference to FIGS. 1-5, the form of the braid may consist of 3 to 16 individual strands. FIGS. 1 and 2 depict the longitudinal appearance of three and four strand braids respectively. In our work, eight strand was the preferred form. The braid pattern may be of the "two-over-one" type, also known as a "plaited sennit". The plaited sennit is depicted by FIG. 3. Braids may also be of the "one-over-one" type. The "one-over-one" style is preferred due to the higher elongation and higher resiliency exhibited by the braid. The eight strand "one-over-one" braid is depicted by FIGS. 4 and 5.

The orthodontically preferred configuration of the braid may be constructed of elastomer monofilament of diameters between 0.003" and 0.040", although the most useful sizes were 0.008" and 0.010" which produced "one-over-one" eight strand braids with OD's of 0.028" and 0.033" respectively, when the monofilament was composed of an aromatic polyester polyether urethane resin.

By changing the tension on the individual filaments, the elongation properties of the final braid could be varied between 150% and 400% with an ultimate elongation of 200–300% being favored.

Examples of braided orthodontic tensioning devices were manufactured from extruded thermoplastic polyurethane elastomer in various diameters. Conventional braiders (New England Butt Company) were used to manufacture braids of various patterns and different numbers of monofilament strands. Commercial braiders are capable of manufacturing braids ranging from 3 to 144 strands.

Example 1—Braiding 0.025" monofilament in a "two-over-one" three strand pattern yielded a rectangular braid with a height of 0.045" and width of 0.065". Similarly, braiding the 0.025" monofilament in a "two-over-one" four strand pattern yielded a square braid with a height and width of 0.070". Elongation of the three and four strand braids to 100% elongation demonstrated both braids were able to retain 69% of their initial load after five minutes at such an elongation, as compared to 62% for the comparable monofilament device.

Example 2—Braiding 0.025" monofilament in an eight strand "two-over-one" pattern yielded a square braid with a width and height of approximately 0.140". The braid exhibited an ultimate tensile load of 7.7 Kg with an ultimate elongation of 390%.

Example 3—Another useful configuration of the braid is one in which at least one strand is a thermoplastic monofilament. Such a braided device is useful for applications in which it is desired to limit the strain or ultimate elongation. A braid made of seven strands of elastomer monofilament of 0.010" diameter and one strand of 0.010" diameter nylon monofilament yielded an eight strand braid with the O.D. of 0.038" when braided in a "one-over-one" pattern. The resultant braid possessed an ultimate tensile force to break of 5.5Kg, with an ultimate elongation of 180%. The addition of more thermoplastic monofilaments will limit the elongation of the braid to a greater extent.

Example 4—Another configuration of braid is one in which one or more strands of monofilament have outside diameters different from the other strands. As an example, an eight strand braid made of two strands of 0.015" O.D. monofilament and six strands of 0.012" O.D. monofilament braided in a "two-over-one" pattern had an O.D. of 0.032". The braid exhibited an ultimate elongation of 225%. Such a configuration improves the tieability of the braid at the expense of its aesthetic properties. The knot strength of such a configuration was 1.6 to 2.0 Kg as compared to 0.8–1.6 Kg for the uniform O.D. strand braid.

Example 5—Two eight strand braids of the "one-over-one" patterns were produced from eight identical strands of extruded polyurethane 0.008" diameter and 0.010" diameter, respectively. A round braid with a small interior hollow was produced in both cases. The outside diameter of the braid made from eight strands of 0.008" monofilament was 0.028" and that made of 0.010" monofilament was 0.033".

Ultimate tensile force to break was 3.6 Kg for the 0.033" braid and 3.0 Kg for the 0.028" braid versus about 2.0 Kg typical for a 0.025" monofilament thread. The hollow nature of the "one-over-one" braid allowed the thread to be tied easily with a standard square knot. A knotted loop of the 0.028" braid would withstand a force of $2.48 \pm 0.18$ Kg before slipping versus $1.57 \pm 0.15$ Kg for a 0.025" monofilament thread. An eight-strand braid of 0.008" strands has an overall outside diameter of D of 0.028" and a combined cross sectional area A of elastomeric material of $4.019 \times 10^{-4}$ square inches. By comparison, a monofilament having an outside diameter of 0.025 has a cross sectional area of $4.906 \times 10^{-4}$ square inches. It is readily apparent from these data that braided strands are of substantially greater strength than a monofilament.

The force retention characteristics of the braided product were compared to conventional thread by stressing the materials in water at 37° C. for a period of six weeks. The 0.028" braid retained 68% of its working force versus 23% for the 0.025" monofilament thread. The force retained is a direct measure of the ability of each device to effect tooth movement in orthodontic treatment.

Figure 6:
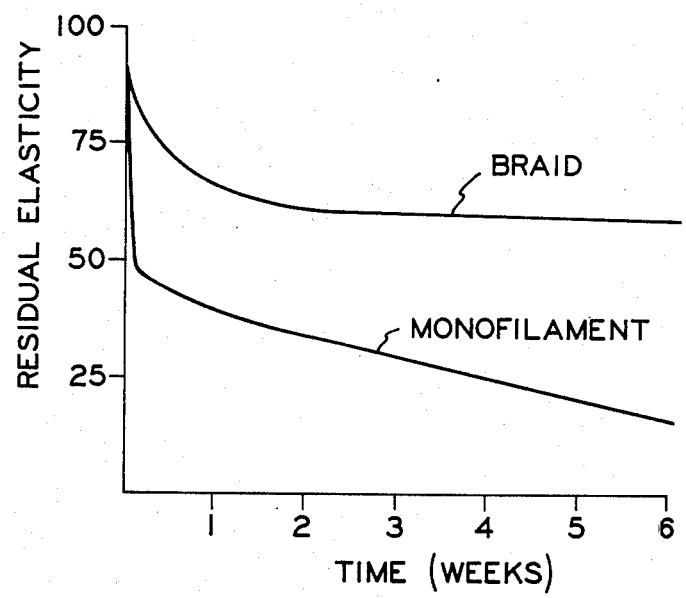
FIG. 6 illustrates the results obtained when residual elasticity is plotted as a function of time. The plot compares the results obtained between the present invention and the prior art.

Referring now to FIG. 6, the comparative curves show the performance of a prior art monofilament with the braid of the present invention. The plot of these curves is percent of residual elasticity (the vertical coordinate) against time in weeks (the horizontal coordinate). As is readily apparent, the prior art monofilament loses its residual elasticity steadily whereas the braided device maintains a nearly flat curve, a nearly constant residual elasticity over the tested time period.

What is claimed is:

1. An orthodontic tensioning thread comprising a braided plurality of elastomeric strands, said plurality of strands having an overall outside diameter D and a combined cross sectional area A of elastomeric material, said strands interacting in tension to import to said thread properties of tensile strength, elasticity retention, tieability, and knot retention greater than corresponding properties of a monofilament of the same material and diameter D having a cross sectional area $\pi D^2/4$ greater than A.

2. An orthodontic tensioning thread according to claim 1 in which said plurality comprises eight monofilament strands.

3. An orthodontic tensioning thread according to claim 1 in which said strands are braided together in a one-over-one braid.

4. An orthodontic tensioning thread according to claim 1 in which said strands are braided together in a two-over-one braid.

* * * * *